United States Patent
Breads et al.

[11] Patent Number: 5,059,118
[45] Date of Patent: Oct. 22, 1991

[54] ORTHODONTIC FINISHING POSITIONER AND METHOD OF CONSTRUCTION

[75] Inventors: Peter R. Breads, Grand Island; Gerard P. Abbatte, Buffalo; Stephen P. Warunek, West Seneca, all of N.Y.

[73] Assignee: Great Lakes Orthodontics, Ltd., Tonawanda, N.Y.

[21] Appl. No.: 384,979

[22] Filed: Jul. 25, 1989

Related U.S. Application Data

[62] Division of Ser. No. 46,087, May 5, 1987, Pat. No. 4,856,991.

[51] Int. Cl.$^5$ .................................................. A61C 3/00
[52] U.S. Cl. ............................................. 433/6; 433/24
[58] Field of Search ................................... 433/6, 24

[56] References Cited

U.S. PATENT DOCUMENTS

| | | | |
|---|---|---|---|
| 3,738,005 | 6/1973 | Cohen et al. | 433/24 X |
| 4,160,322 | 7/1979 | Frazier | 433/24 |
| 4,183,141 | 1/1980 | Delliger et al. | 433/24 |
| 4,284,405 | 8/1981 | Dellinger | 433/24 |
| 4,526,540 | 7/1985 | Dellinger | 433/24 |
| 4,551,096 | 11/1985 | Dellinger | 433/24 |
| 4,591,341 | 5/1986 | Andrews | 433/6 |
| 4,793,803 | 12/1988 | Martz | 433/6 |

*Primary Examiner*—Robert P. Swiatek
*Assistant Examiner*—Nicholas D. Lucchesi
*Attorney, Agent, or Firm*—Hodgson, Russ, Andrews, Woods & Goodyear

[57] ABSTRACT

An orthodontic finishing positioner for maloccluded teeth to which are secured coupling members having portions protruding from the sides of the teeth includes a body constructed of an elastomer base material adapted to be operatively positioned about the teeth and coupling member of at least one dental arch of a patient. The positioner body is arcuate in shape and defines a recess for receiving teeth of at least one dental arch wherein the recess includes walls defining teeth-engaging surfaces shaped generally complementary to the surfaces of the teeth of the one dental arch when the teeth therein are positioned in a predetermined or ideal orientation. The recess walls further defines a series of indentations disposed across the teeth-engaging surfaces wherein each indentation being shaped to nestingly accept a corresponding coupling member so that when the positioner body is operatively positioned within the patient's mouth and stretched about the teeth of the one dental arch so that the teeth thereof are operatively received by the recess of the arcuate-shaped portion and each coupling member is accepted by a corresponding indentation, the stretched body effectively grasps the teeth and acts against the teeth and the coupling member to bias the teeth of the one arch toward the predetermined orientation. The method of the invention includes the steps involved in constructing the positioner of the invention. Such construction steps include the constructing of an impression-formed model of the teeth and coupling members of the one dental arch, repositioning the teeth-simulating portions of the model to a predetermined orientation and utilizing the model, with its repositioned teeth-simulating portions, as a standard for the formation of the desired positioner.

18 Claims, 5 Drawing Sheets

Fig. 11.
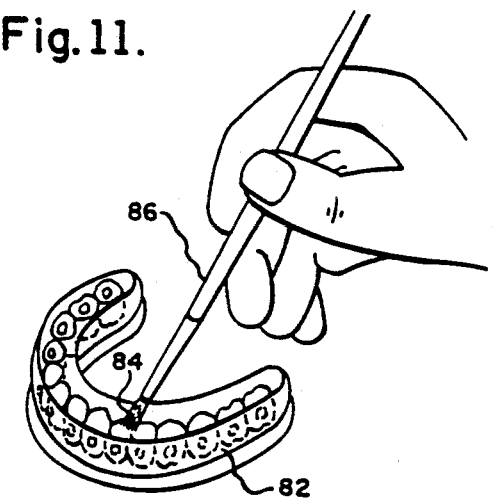
Fig. 14.
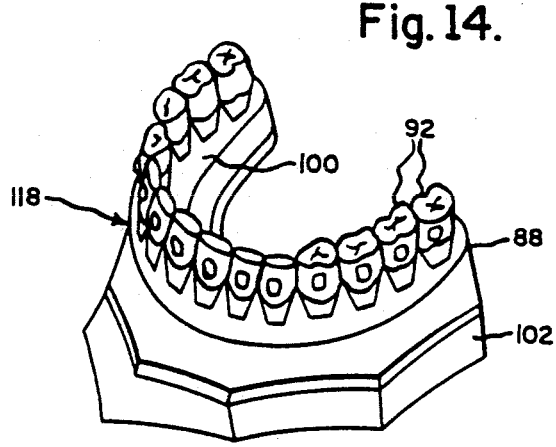
Fig. 12.
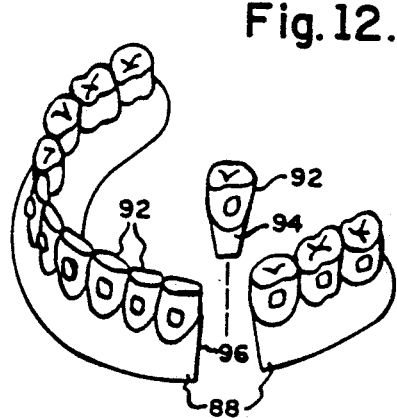
Fig. 15.
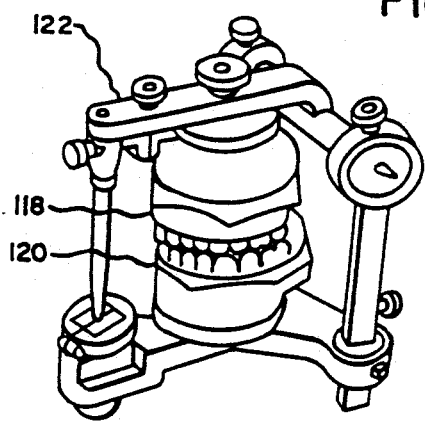
Fig. 13.
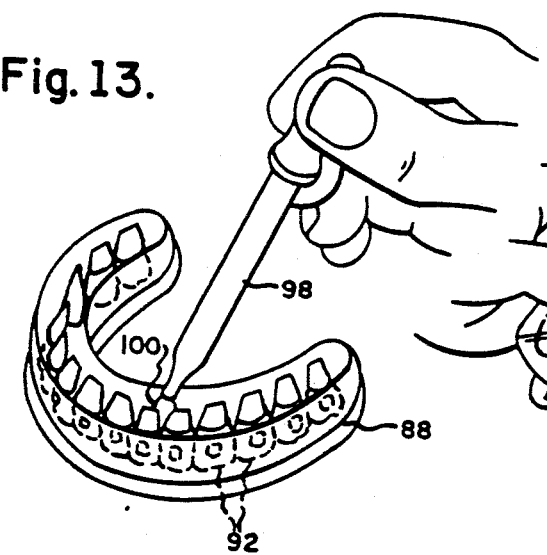
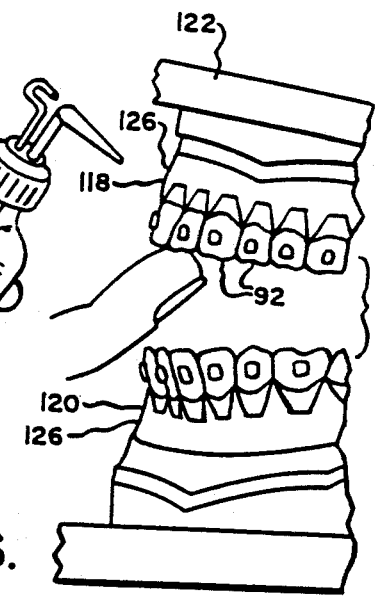
Fig. 16.

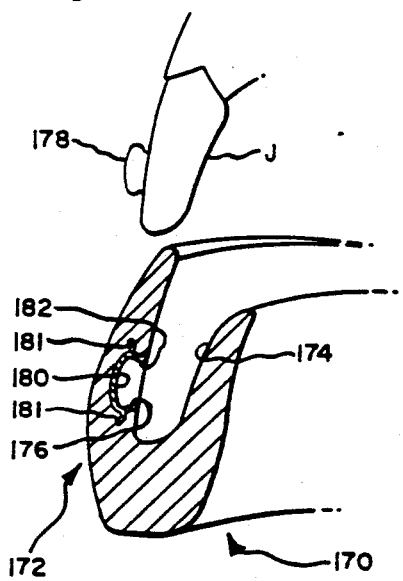
Fig. 24.
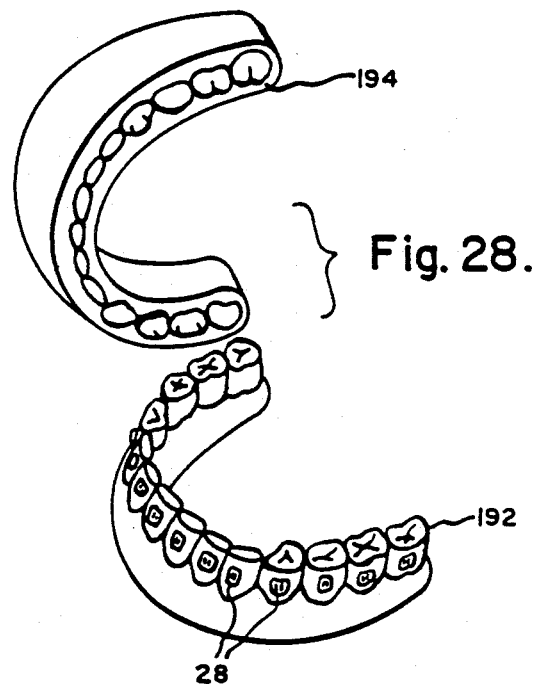
Fig. 28.
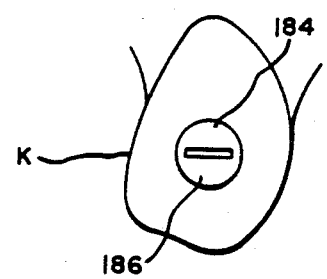
Fig. 25.
Fig. 29.
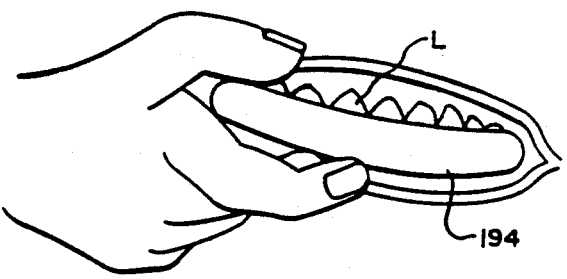
Fig. 26.
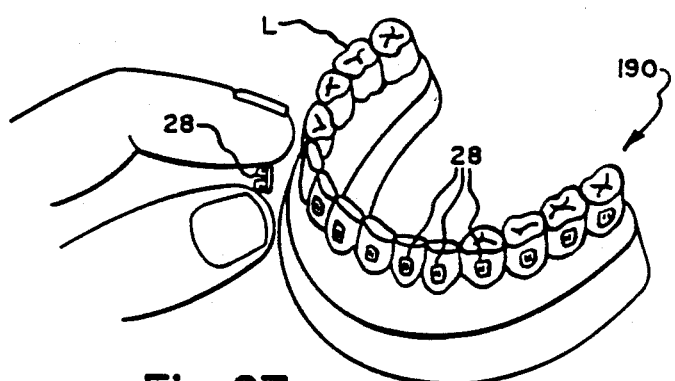
Fig. 27.

ORTHODONTIC FINISHING POSITIONER AND METHOD OF CONSTRUCTION

This is a divisional of co-pending application Ser. No. 07/046,087 filed on May 5, 1987, now U.S. Pat. No. 4,856,991.

BACKGROUND OF THE INVENTION

This invention relates generally to the orthodontic treatment of maloccluded teeth and relates more particularly to a tooth positioner and an associated method of constructing the positioner.

In order to reposition a patient's teeth to a desired orientation, it is known that a positioner constructed of an elastic material and having an appearance resembling a common mouthguard can be operatively positioned about the patient's teeth for urging ones of the teeth toward a predetermined or desired position. It is also known that for the purpose of positively locking the positioner within the patient's mouth, suitable coupling members can be attached to the teeth of a patient for mating and coacting with the positioner. An example of such a positioner for use in connection with tooth-mounted coupling members is shown and described in U.S. Pat. No. 3,407,500.

It is an object of the present invention to provide a new and improved finishing positioner constructed of elastomer base material for use on teeth to which coupling members have been attached for coacting with the coupling members for biasing preselected ones of the teeth to a predetermined or desired occlusion and an associated method of constructing the positioner.

Another object of the present invention is to provide such a positioner for transferring elastic force potential of the elastomer base material to the preselected teeth with enhanced effectiveness and efficiency.

Still another object of the present invention is to provide such a positioner which cooperates with retaining brackets of the type commonly used in connection with arch wires for transferring elastic force potential to the teeth through the retaining brackets.

Yet still another object of the present invention is to provide such a positioner for providing a biasing force to preselected teeth within a range of force levels commonly accepted by orthodontic practitioners for repositioning teeth.

A further object of the present invention is to provide such a positioner which is economical to construct.

A still further object of the present invention is to provide such a method for effectively capturing bracket detail in the body of the resulting positioner.

SUMMARY OF THE INVENTION

This invention resides in an orthodontic appliance or positioner and an associated method of construction for realigning maloccluded teeth of a patient to a predetermined orientation, to which teeth are secured coupling members for coacting with the positioner.

The positioner of the present invention is comprised of a body constructed of an elastomer base material having an arcuate-shaped portion along which is defined a recess for receiving teeth of one dental arch of the patient and wherein the teeth of the one dental arch include maloccluded teeth to which are secured coupling members having portions protruding from the sides of the teeth. The recess includes walls defining teeth-engaging surfaces shaped generally complementary to the surfaces of the teeth of the one arch when the maloccluded teeth thereof are positioned in a predetermined orientation. The recess walls further define a series of indentations disposed across the teeth-engaging surfaces wherein each indentation is in the form of an open-sided cavity shaped to nestingly accept a corresponding coupling member when placed thereabout so that when the positioner body is operatively positioned within the patient's mouth and stretched about the teeth of the one dental arch so that the teeth thereof are operatively accepted by the recess and each coupling member is operatively and nestingly accepted by a corresponding indentation, the stretched body acts against the teeth and the coupling members to effectively bias the teeth of the one arch toward the predetermined orientation.

The method of the invention includes the steps involved in constructing the positioner of the invention. Provided for the construction is a hardened dental facsimile formed from an impression of the preselected dental arch and coupling members wherein the dental facsimile includes portions simulating the teeth and a portion of the gum tissue adjacent the teeth of the preselected dental arch and the surfaces of the coupling members are defined by the surfaces of either coupling member-simulating portions of the facsimile or coupling members attached to the teeth-simulating portions of the facsimile. The teeth-simulating portions of the facsimile are then repositioned to a preselected orientation to provide a first model of the preselected dental arch having teeth-simulating portions oriented in the same manner as the teeth in the preselected arch are desired to be positioned. An amount of elastomer base material is then provided, and the positioner is subsequently formed out of the elastomer base material so that the positioner assumes a body having an arcuate-shaped portion along which is defined a recess shaped in conformity to the shape of the facsimile so as to include walls defining teeth-engaging surfaces for receiving the teeth-simulating portions of the first model and a series of indentations disposed across the teeth-engaging surfaces and wherein each indentation is shaped to nestingly accept a corresponding coupling member surface defined upon the first model. Because the positioner body recess is constructed in conformity to the shape of the facsimile, the operative positioning of the positioner body within the patient's mouth so that the teeth of the preselected arch are received by the teeth-engaging surfaces and the coupling members mounted therein are nestingly received by the indentations places the positioner body is in a stretched condition therein so that the positioner body acts against the teeth and coupling members to bias the teeth of the one arch toward the predetermined orientation.

BRIEF DESCRIPTION OF THE DRAWING FIGURES

FIG. 11 is a perspective view illustrating the application of an uncured die stone material to the FIG. 10 impression for forming a die stone facsimile of the patient's teeth.

FIG. 12 is a perspective view illustrating a preselected one of the teeth-simulating portions of a die stone facsimile formed with the FIG. 10 impression having been cut from the remainder of the facsimile and having its root portion narrowed to somewhat of a V-shape.

FIG. 13 is a perspective view illustrating the application of wax to the teeth-simulating portions when operatively repositioned in the FIG. 10 impression to form a reconstructed facsimile of the patient's teeth.

FIG. 14 is a perspective view of the teeth-simulating portions of FIGS. 12 and 13 together with the added wax of FIG. 13 shown mounted upon a base to form a combination wax/stone model of the patient's teeth.

FIG. 15 is a perspective view of combination wax/stone models of the teeth of both the upper and lower dental arches shown operatively mounted within a dental articulator.

FIG. 16 is a perspective view of the articulator-mounted models of FIG. 15 illustrating the repositioning of teeth-simulating portions of the models to preselected orientations.

FIG. 24 is an elevation view, shown in section, of another alternative embodiment of a positioner in accordance with the present invention shown in condition for operative placement upon the teeth of a patient.

FIG. 25 is a perspective view of a retaining bracket having an alternative construction to those illustrated in FIGS. 5a and 5b and shown operatively positioned upon a tooth.

FIG. 26 is a perspective view illustrating the obtaining of a dental cast of the upper dental arch of a patient.

FIG. 27 is a perspective view of a dental facsimile to which retaining brackets are being mounted.

FIG. 28 is a perspective view of the bracket-bearing facsimile of FIG. 27 and a transfer matrix formed from the facsimile.

FIG. 29 is a perspective view of the transfer matrix of FIG. 28 being used to operatively locate the retaining brackets of the bracket-bearing facsimile within the patient's mouth.

DETAILED DESCRIPTION OF THE ILLUSTRATED EMBODIMENTS

Figure 1:
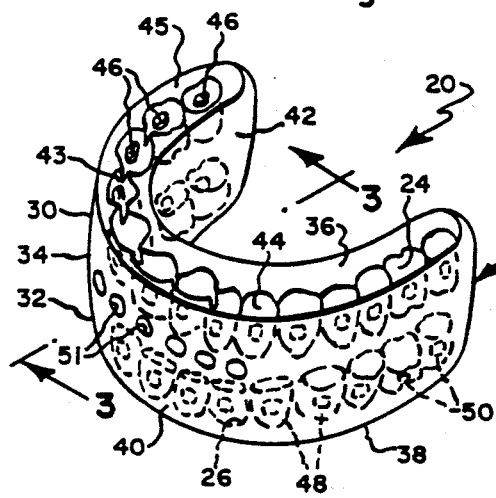
FIG. 1 is a perspective view of an embodiment of a positioner in accordance with the present invention.

Turning now to the drawings in greater detail and considering first FIGS. 1-4, there is shown an orthodontic finishing appliance or positioner, generally indicated 20, in accordance with the appliance of the present invention for repositioning maloccluded teeth T (FIG. 4) of a patient P to a predetermined orientation and to which teeth T coupling members 21 have been attached. Inasmuch as the positioner 20 is a finishing positioner, it is particularly well-suited for repositioning maloccluded teeth after conventional bands and arch wires have been used to initiate treatment. As will be explained in detail hereinafter, the positioner 20 cooperates with the coupling members 21 carried by maloccluded teeth to urge the teeth to the predetermined orientation.

Although the teeth-mounted coupling members 21 can take any of a number of forms in the interest of this invention as will be hereinafter discussed, the coupling members 21 are in the form of retaining brackets 28 of the type commonly used in connection with arch wires (not shown) of orthodontic braces. Therefore, while the ensuing discussion addresses the utilization and/or construction of the positioner 20 about retaining brackets 28, it will be understood that the type of coupling members 21 with which a positioner in accordance with the present invention can be used is not limited to retaining brackets of this type.

The positioner includes a unitary body 22 constructed of an elastomer base material having a pair of teeth-accepting recesses 24, 26 for closely and snugly accepting the teeth to which retaining brackets 28 (FIG. 4) are secured. The recesses 24, 26 are shaped in conformity to the general contours of the teeth T and brackets 28 when the teeth T are oriented in a predetermined or desired orientation. Therefore, when the positioner 20 is operatively positioned about the maloccluded teeth T, the body 22 is in a stretched or deformed condition and the elasticity of the body 22 biases the teeth T toward the predetermined orientation.

Figure 2:
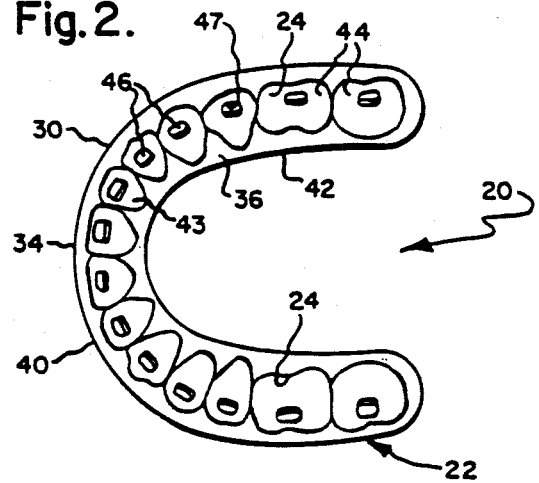
FIG. 2 is a plan view of the FIG. 1 positioner as seen generally from above in FIG. 1.
Figure 3:
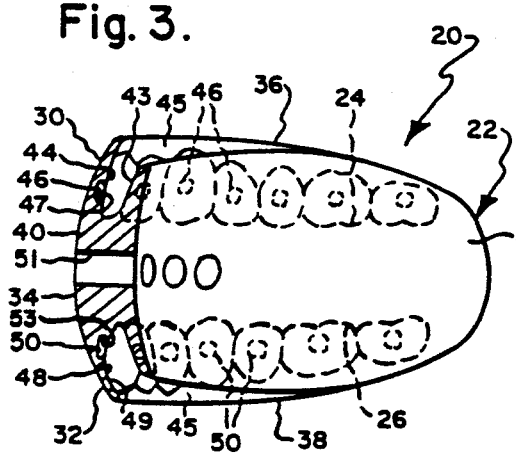
FIG. 3 is a cross-sectional view taken about on lines 3—3 of FIG. 1.

With reference still to FIGS. 1-3, the positioner 20 includes means defining a first, or upper, portion 30 and means defining a second, or lower, portion 32 between which is sandwiched a mid-portion 34. Each of the upper, lower and mid-portions 30, 32, 34 are generally arcuate in shape as viewed in the plan view of FIG. 2 so that the arc thereof generally conforms to that of the upper and lower dental arch of the patient P. Furthermore and in the positioner embodiment 20, the unitary body 22 provides each of the means defining the upper portion 30, the means defining the lower portion 32 and the mid-portion 34.

The positioner body 22 defines a top side 36, a bottom side 38 and an outwardly-directed surface 40 and an inwardly-directed surface 42 extending between the top and bottom sides 36, 38. The recess 24, mentioned earlier, is defined in the top side 36 of the body 22 is of such shape and size to cooperatively receive the teeth T and retaining blocks 28 of the upper dental arch, indicated U in FIG. 4, of the patient when the teeth T are oriented in a predetermined orientation. More specifically, the recess 24 includes walls 43 defining teeth-engaging surfaces 44 shaped generally complementary to the surfaces of the teeth T of the upper arch when preselected ones of the teeth of the upper arch U are positioned in a corrected or idealized orientation. Furthermore, the recess walls 43 define a series of indentations 46 disposed across the teeth-engaging surfaces 44 wherein each indentation 46 is shaped to nestingly accept a corresponding retaining bracket 28 of the upper dental arch U when operatively positioned thereabout. As best shown in FIG. 3, each indentation 46 is in the form of an open-sided or cuplike cavity having an opening shaped generally in conformity to the projected outline or shape of the retaining bracket 28 which the indentation 46 is adapted to accept and defines an interior surface 47 shaped generally complementary to the general shape of the bracket 28 so that when the indentation 46 is operatively stretched about the bracket 28, the interior surface 47 closely surrounds the bracket 28 and indentation opening or more specifically, the edge thereof, closely encircles the bracket 28.

Figure 4:
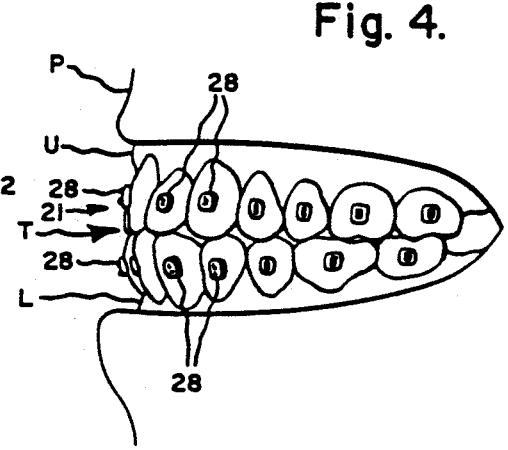
FIG. 4 is a perspective view of patient's teeth about which the FIG. 1 positioner has been designed to be operatively positioned.

The recess 26 is defined in the bottom side 38 and in the lower portion 32 of the positioner body 22 and includes walls 49 defining teeth-engaging surfaces 48 shaped generally complementary to the surfaces of the teeth T of the lower dental arch, indicated L in FIG. 4, of the patient when the teeth T therein are positioned in a preselected or corrected orientation. Furthermore, the recess walls 49 define a series of indentations 50 disposed across the teeth-engaging surfaces 48 wherein each indentation 50 has an interior surface 53 is shaped to nestingly accept a corresponding retaining bracket 28 of the lower dental arch L when the indentation 50 is operatively positioned about a bracket 28 wherein the interior surface 53 completely and snugly surrounds the bracket 28.

Each of the recess walls 43 or 49 further defines gum-engaging surfaces 45 adjacent the teeth-engaging surfaces 44 or 48 for engaging a portion of the gum tissue G located adjacent the teeth T when the positioner 20 is operatively worn. The gum-engaging surfaces 45 are shaped generally complementary to the surface of the gum tissue over which the surfaces 45 are adapted to engage so that when the positioner 20 is operatively worn, the gum-engaging surfaces 45 lie comfortably against the gum tissue.

The mid-portion 34 spaces the recesses 24, 26 from one another so that when the positioner 20 is operatively positioned within the mouth and the upper and lower teeth T are operatively received by the recesses 24, 26, the teeth of the upper and lower dental arches U, L, respectively, are arranged in an open bite relationship. Furthermore, the mid-portion 34 defines a plurality of through-apertures 51, 51 extending between the outwardly and inwardly-directed surfaces 40 and 42 to facilitate breathing through the mouth while the positioner 20 is worn by the patient P.

When the positioner 20 is operatively positioned within the mouth so that the body 22 is operatively stretched about the patient's teeth T and brackets 28, each recess 24 or 26 nestingly and operatively receives the teeth of the corresponding arch U or L in a relatively snug fit-up relationship and each indentation 46 or 50 nestingly and operatively receives a corresponding retaining bracket 28. Inasmuch as the actual position of the teeth T is not the same as the predetermined, or corrected, orientation of the teeth T, it will be understood that the positioner body 22 is in a stretched or deformed condition when operatively positioned about the teeth T. The elasticity or memory of the body 22 thereby effectively biases the maloccluded teeth T toward the predetermined or preselected orientation as the body 22 attempts to return to its relaxed or undeformed condition.

The material out of which the positioner body 22 is constructed can be any of a number of elastomer base materials. It has been found, however, that an elastomer base material available under the trade designation Silastic Q7-4840 from Dow Corning Corp., Midland, Mich. provides the body 22 with a suitable degree of resiliency, elasticity, and flexibility. Furthermore, it is believed that the biasing force exerted upon teeth T by the elasticity of the body 22 constructed of Silastic Q7-4840 is within a range of force levels commonly accepted by orthodontic practitioners for repositioning teeth.

An advantage provided by the positioner 20 relates to its ability to grasp the maloccluded teeth T for the purpose of transferring elastic force potential from the positioner 20 to the teeth. To this end, the indentations 46, 50 of the teeth-engaging surfaces 44 and 48 are stretched about so as to nestingly accept the retaining brackets 28 and the remainder of the teeth-engaging surfaces 44 and 48 are stretched about so as to nestingly accept the crowns of the teeth T when the positioner 20 is operatively positioned within the mouth. Hence, the indentations 46, 50 coact as male and female couplers, respectively, to enhance the securement of the body 22 to the teeth T and cooperate to provide an effective grasping of the brackets 28 by the body 22. Such an effective grasping of the brackets 28 is believed to enhance the transfer of elastic force potential from the positioner 20 to teeth T and to thereby efficiently utilize the elasticity of the positioner body 22.

Figure 5A:
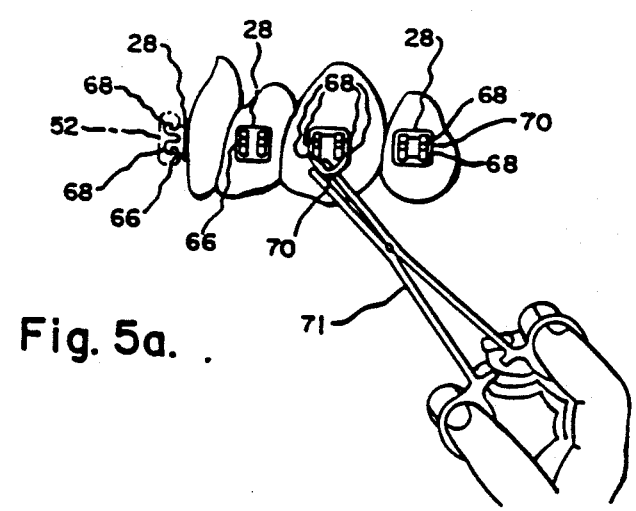
FIG. 5a is a perspective view of the patient's teeth as shown in FIG. 4 but drawn to a slightly larger scale and illustrating a step in preparing the patient's teeth prior to the making of an impression thereof.
Figure 5B:
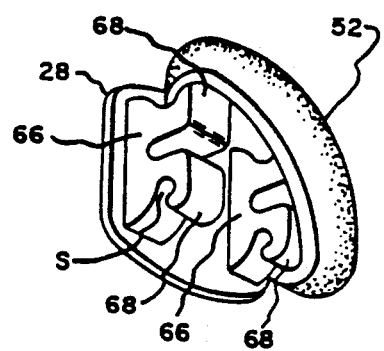
FIG. 5b is a perspective view of a cap-like body in condition for operative placement about a retaining bracket.

The method of the present invention includes the steps involved in constructing the positioner 20. Initially, the patient's mouth is prepared for the making of impressions of the teeth located in the upper and lower dental arches from which die stone models of the teeth are formed in a manner hereinafter described. If the patient is wearing the arch wires of his orthodontic braces, the arch wires are removed to suitably expose the retaining brackets 28. Each bracket 28, as best shown in FIGS. 5a and 5b, includes a block-like body 66 suitably glued to its corresponding tooth and substantially centrally of the buccal surface of the tooth. Furthermore, each bracket 28 includes four tie wings 68, 68 protruding from the corners of the body 66 as shown in FIGS. 5a and 5b so that an undercut or spacing, indicated S, is defined between the tie wings 68, 68 and the base of the bracket body 66. It will be understood, however, that an alternative bracket which is functionally comparable to the illustrated bracket 28 may include a number of tie wings other than four such as, for example, two.

Inasmuch as each tie wing 68 or 68 of the brackets 28 is relatively sharp, each bracket 28 is then suitably covered so that impression material subsequently applied about the teeth T and brackets 28 is not appreciably torn or damaged upon removal of the impression material from the teeth T by the bracket tie wings 68, 68 and so that impression material which is subsequently applied to the brackets 28, 28 in a manner hereinafter described does not become lodged within the spacing S. It has been found that the brackets 28 can be suitably covered for the aforesaid purposes by at least two techniques. For example and with reference to FIGS. 5a and 5b, the brackets 28, 28 may be suitably covered by a cap 52 having a cup-like body adapted to be stretched into place about a bracket 28 so as to cover all four tie wings 68, 68. The cup-like body of the cap 52 has an outer configuration which is somewhat rounded in shape so that when operatively stretched about a bracket 28 as illustrated in phantom in FIG. 5a, the cap 52 effectively provides the sharp corners of the tie wings 68, 68 with a smooth, rounded covering and thickens the bracket body 66. An example of such a cap 52 is available under the trade designation HUG CAP from Kreative Koncepts, Inc. of Hinsdale, Ill.

The brackets 28, 28 may also be suitably covered by tightly wrapping the block-like body 66 of each bracket 28 with an elastic or rubber band 70. In such an instance and as illustrated in FIG. 5a, rubber band 70 can be wrapped about a corresponding bracket 28 by means of an appropriately-shaped instrument such as a hemostat 71. The resultant rubber band wrapping effectively thickens the body 66 to thereby fill the spacing S and provides each bracket body 66 with a built-up outermost surface so that the outermost edges of the tie wings 68, 68 are substantially even with the outermost surface of the wrapped rubber band 70 and so that only the generally-projected outline or shape of each bracket 28 is presented for impression-making purposes. Furthermore, the brackets 28, 28 can be suitably covered by means of an elastic-like ring of the type available under the trade designation G MODULES and available from Unitek Corp., Monrovia, Calif. Such a ring is adapted to be stretched about so as to encircle the body 60 of the bracket 28 and be received by so as to substantially fill the retainer wire-accepting slot extending laterally across the bracket 28.

If the patient's orthodontic braces also include buccal tubes (not shown), it is necessary during the preparation of the patient's mouth to either remove the buccal tubes from the teeth or to fill the tubes so that impression materials subsequently applied to and around the tubes cannot become lodged therein. It has been found that wax or a wax-like lip balm can be used to suitably fill the buccal tubes.

Once the patient's mouth has been suitably prepared as aforedescribed, and with reference to FIGS. 6 and 7, an impression is formed of a preselected one of the patient's dental arch, such as the upper arch U, with which a die stone facsimile or model of the arch is subsequently formed. Such an impression can be formed by providing an impression material, indicated 74, for accurately capturing the shape and contour of the teeth T and brackets 28 when applied thereto. An example of acceptable impression materials include that which is available under the trade designation BONDO SIL from Ortho-Bonding Co., Del Ray Beach, Fla., BONDO SIL is comprised of a base putty and a liquid catalyst and is prepared by initially spreading an amount of base putty onto a mixing pad or glass and scored so as to form crisscrossing lines thereacross. The liquid catalyst is then applied over the crisscrossing lines, and the amount 72 is folded and kneaded briskly to obtain homogeneity.

Figure 6:
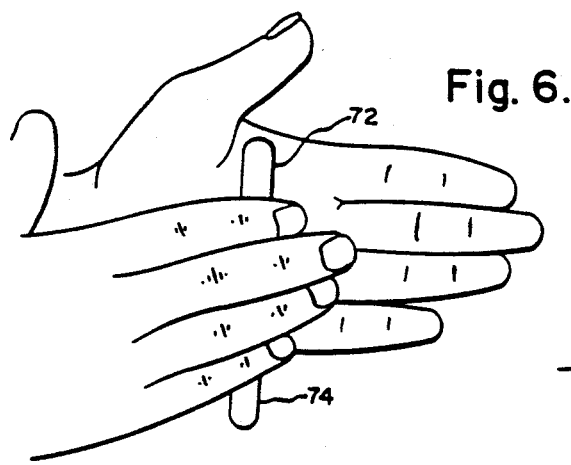
FIG. 6 is a perspective view of an amount of impression material being prepared for making an impression of the teeth located in one of the patient's dental arches.
Figure 7:
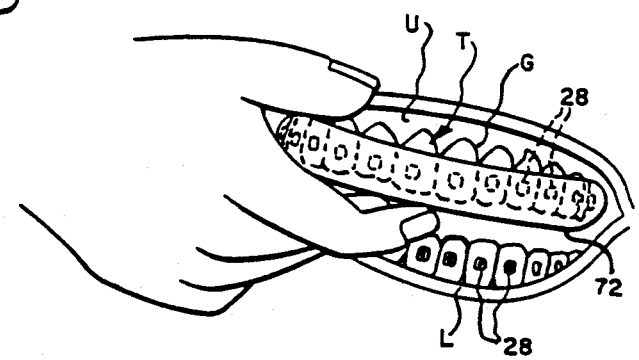
FIG. 7 is a perspective view illustrating the FIG. 6 impression amount being operatively applied to and pressed about the teeth of the patient's dental arch.

If the impression material 74 is BONDO SIL and with reference to FIG. 6, a first amount 72 of impression material is provided and then rolled between the hands, as shown in FIG. 6, to conform the amount 72 to somewhat the shape of an elongated cylinder. Inasmuch as the cylindrically-formed amount 72 will be subsequently layered or pressed upon the crowns of the teeth T of the upper arch U, the length of the cylindrically-formed amount 72 is about equal to that of the arc of the upper arch U. At that point, the cylindrically-formed amount 72 of material 74 is bent in conformity to the arc of the upper dental arch U, inserted within the mouth and pressed upon the teeth T. The amount 72 is then shaped about the teeth T and brackets 28 in the upper dental arch U by manually pushing and thereby moving the impression material 74 about, so as to cover, the surfaces of the teeth T, retaining brackets 28 and a portion of the gum tissue G adjacent the teeth T. In practice, it is preferred that the impression material 74 be forced to overlie all of the gum tissue G within 0.25 inches (0.6 cm) of the teeth T so that the shape of a substantial portion of the gum tissue G is accurately captured by the impression material 74. The impression material 74 is then permitted to cure by, for example, the passage of an appropriate period of time while the impression material 74 remains in position about the teeth. A first amount of BONDO SIL commonly requires about four to five minutes of setting time.

While the first amount 72 of BONDO SIL is operatively pressed about the teeth T as aforedescribed, portions of the first amount 72 may rupture to thereby expose some of the teeth T or brackets 28 through the first amount 72. If this occurs, the exposed teeth T or brackets 28 need not be covered prior to the curing of the first amount 74.

Figure 8:
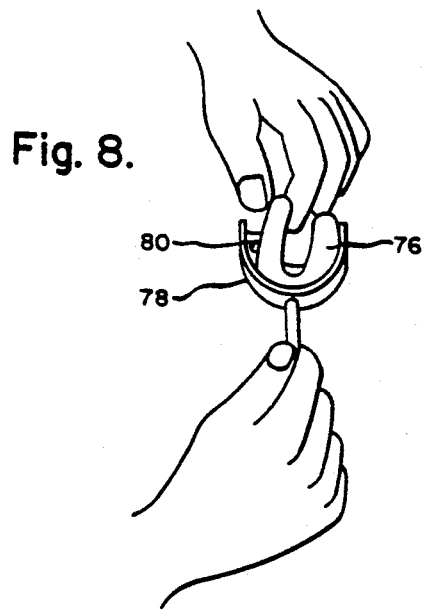
FIG. 8 is a perspective view of a second amount of impression material being positioned upon a matrix fork.

With reference to FIG. 8, a second amount, indicated 76, of BONDO SIL is then prepared in a manner identical to that of the first amount 72, as described above, and conformed or rolled with the hands into somewhat the shape of an elongated cylinder having a length which is about equal to the length of the arc of the upper dental arch U. A matrix fork 78 is then provided and the second amount 76 is then pressingly applied to one side, or the upper side as shown in FIG. 8, of the fork 78 so that the second amount 76 extends substantially along the entire length of the arc of the fork 78. The matrix fork 78 defines a series of holes 80 (only one shown in FIG. 8), as shown, and the operative pressing of the amount 76 onto the fork 78 as aforedescribed commonly forces portions of the second amount 76 to protrude through the holes 80 from the upper side of the fork 78.

Figure 9:
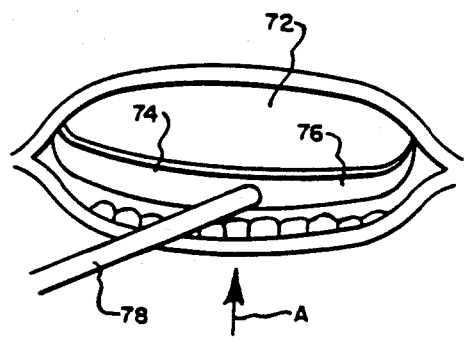
FIG. 9 is a perspective view illustrating the FIG. 8 impression amount being operatively applied to the underside of the FIG. 6 amount which had previously been applied to the teeth as shown in FIG. 7.
Figure 10:
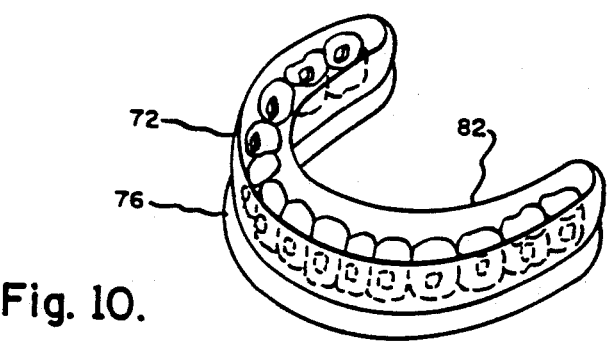
FIG. 10 is a perspective view of the cured unitary impression taken of the teeth of the patient in accordance with the steps illustrated in FIGS. 5-9 shown removed from the mouth.

With reference to FIG. 9, the second amount 76 of BONDO SIL is then applied to the first amount 72 by inserting the fork 78 into the mouth and pressing the amount 76 against the teeth T of the upper arch U in the direction of the arrow A. The second amount 76 is thereby pressed in underlying relationship with the first amount 72 so that each end of the arc of the second amount 76 generally corresponds with an end of the arc of the first amount 72 and so that the first and second amounts 72 and 76 effectively bond or adhere to one another. Excess material of the second amount 76 rendered available from the pressing of the second amount 76 upon the first amount 72 is then spread or smeared across the first amount 72 so as to cover any exposed teeth T or brackets 28. The second amount 76 is then permitted to cure so that the first and second amounts 72, 76 collectively form the desired impression, indicated 82 in FIG. 10, of the upper dental arch U. The resultant unitary impression 82 is relatively soft and rubbery and is substantially strengthened by the inclusion of the second amount 76 of impression material 74.

Upon curing of the second amount 76 of BONDO SIL, the matrix fork 78 is removed from the mouth and the impression 82 is removed from the teeth T. Commonly, the removal of the impression 82 from the mouth necessitates a stretching of the impression material so that the impression 82 clears the details of the teeth T and retaining brackets 28. Because the brackets 28 have been covered as aforedescribed, the likelihood that the impression 82 will tear or be otherwise damaged from the sharp corners of the tie wings 68 is substantially reduced. Once removed from the teeth T, the impression 82 should be checked to be sure that no undesirable voids have been formed therein. Preferably, the impression 82 should also be replaced upon the matrix fork 78 and the aforedescribed protruding portions of the second amount 76 repositioned through the matrix fork holes 80,80 to ensure that there is no distortion of the impression 82 when repositioned upon the fork 78. Inasmuch as the impression 82 is to provide an accurate impression of the detail of the teeth T and brackets 28, any impression inaccuracies or damage which would subsequently prevent the obtaining of an accurate model of the teeth and brackets 28 formed from the impression 82 would require that a new and replacement impression be taken.

As an alternative to using BONDO SIL as the impression material 74, an alginate composition of the type commonly used to form alginate impressions, can also be used to form a suitable impression of the patient's dental arch. Such steps in the formation of an alginate impression of a patient's dental arch are well known in the art. Briefly, however, and with regard to the making of an alginate impression of the bracketed teeth T of the patient P, an amount of uncured alginate composition is spatulated into a suitably-sized impression tray, the impression tray is inserted into the mouth and the alginate composition appropriately seated unto the teeth T. Because the uncured alginate composition is relatively liquid, the alginate composition flows around the teeth and brackets to effectively capture the detail of the shape and contour of the teeth T and brackets 28. The alginate composition is subsequently permitted to set and then removed from the teeth by gently rocking the impression tray to break the suction seal commonly formed between the teeth and alginate material and subsequently directed off of the teeth and out through the mouth. As was the case with the BONDO SIL impression, the alginate impression is not appreciably damaged to the extent rendering the impression unusable as the impression is pulled over the brackets 28 upon removal of the impression from the mouth.

With reference to FIG. 11, a die stone composition, indicated 84, and in an uncured condition is provided and placed within the impression 82 to form a hard, die stone facsimile of the patient's teeth T, retaining brackets 28 and gum tissue G. An example of a die stone material out of which the die stone facsimile can be formed is available under the trade designation VEL MIX STONE from Kerr/Division of Sybron Corp., Romulus, Mich. Prior to being placed within the impression 82, the die composition 84 is vacuum-spatulated to remove air bubbles and is subsequently placed within the impression 82 by means of a brush 86 and a spatula (not shown). Initially the bristles of the brush 86 are used to scoop amounts of the composition 84 from its container and brush-apply the composition amounts to the impression 82 until the teeth-simulating portions of the impression 82 are filled with the composition 84. The remainder of the impression 82 is then filled with composition 84 as a spatula is used as a scoop. The die stone composition 84 is then permitted to cure to the desired hardened condition. To maximize model detail, the die stone composition 84 is preferably cured in a pressure vessel in room temperature. The hardened facsimile, indicated 88 and shown inverted in FIG. 12, is then removed from the impression 82 by stretching the impression 82 over and off of the detail of the facsimile 88. Inasmuch as the impression 82 is used again during the construction of the positioner 20 as will be described hereinafter, care should be taken during the removal of the impression 82 from the facsimile 88 so as not to destroy the impression 82.

With reference still to FIG. 12, the portions of the facsimile 88 simulating the teeth T and which are desired to be repositioned to a predetermined orientation are each separately cut or sawed from the remainder of the facsimile 88. In the facsimile 88 and as exemplified by the tooth-simulating portion 92 shown isolated in FIG. 12, the portions 92,92 of the facsimile 88 simulating the anterior and positioner teeth of the upper dental arch U are each cut from the remainder of the facsimile 88 in the dental interproximal area thereof and shaped in the root area thereof so that each tooth-simulating portion has a V-shaped or wedge-like base 94. To separate each portion 92, a cut is initiated along the desired path and the facsimile 88 is broken in two along the initiated cut, and the shaping of the root area of each portion 92 can be performed by means of a cutting disk which is mounted on a bench lathe.

Once the portions 92,92 are separated from one another and shaped as aforedescribed, each portion 92 is repositioned in the unitary impression 82 (FIG. 10) in the location therein at which the corresponding portion 92 was formed when the facsimile 88 was made. Because the contours of the tooth of each portion 92 was formed in accordance with the contours of the interior walls of the impression 82, the portions 92,92 engage the impression walls so that the walls of the impression 82 effectively support the portions 92,92 in an upright condition in the impression 82 as shown in FIG. 13.

With reference still to FIG. 13 and with cutout portions 92,92 repositioned within the impression 82, wax, indicated 100, is then warmed and applied, by means of a dropper 98, within the impression 82 so that the V-shaped base 94 of each portion 92 is surrounded by wax 100. Once the wax 100 is permitted to cool, the portions 92,92 are thereby secured therein. Inasmuch as the wax 100 is intended to simulate gum tissue which can be manipulated in a manner hereinafter described, it is preferred that the portions 92,92 be covered with wax to a depth of about two to three millimeters. The warm wax 100 is thereafter permitted to cool, and the remainder of the impression 82 is filled with an uncured die stone composition. The surface of the wax 100 which is intended to be overlain by the subsequently-applied die stone composition is preferably roughened or grooved so that the overlying die stone forms an effective bond with the underlying wax.

The die stone composition is added to the impression 82 so that the reconstructed facsimile, or combination wax/stone model 118 (FIG. 14), has sufficient bulk out of which a mounting base can be formed. To form the mounting base, indicated 102 in FIG. 14, the die stone composition is liberally applied atop the wax 100, permitted to cure, removed from the impression 82 with the wax 100 and teeth-simulating portions 92 attached thereto, and subsequently trimmed with a model trimmer to the desired shape. The resultant wax/stone model 118 is, in essence, a reconstructed facsimile of the patient's upper dental arch U.

In the manner in which the wax/stone model 118 was constructed to form a model of one of the upper dental arch U (FIG. 4), a second wax/stone model is formed of the other dental arch L. Briefly, an impression is made of the teeth T and retaining brackets 28 of the lower dental arch L, a die stone facsimile is formed from the impression, the teeth-simulating portions of the facsimile are separated from and repositioned in the impression of the lower arch L, and a reconstructed facsimile of the upper arch L is formed by applying wax within the lower arch impression and liberally applying an uncured die stone composition to the applied wax. The die stone is thereafter permitted to cure to a hardened condition, the reconstructed facsimile including die stone teeth-simulating portions, overlying wax and the liberally-applied die stone composition is removed from the lower arch impression and the liberally-applied die stone composition is trimmed to form a base of desired shape. The reconstructed facsimile thereby provides the combination wax/stone model 120 (FIG. 15) simulating the teeth, brackets and gum tissue of the lower dental arch L.

As shown in FIG. 15, both wax/stone models 118,120 are then operatively positioned within a dental articulator 122. To ensure the proper index or bite relationship between the models 118,120, a wax bite and a maxilliary cast are made of the patient's mouth and appropriate adjustments are made to the articulator 122 in accordance with the recorded wax bite and maxilliary cast and in accordance with standard face bow transfer techniques. The methods and procedure for obtaining a wax bite and maxilliary cast of the patient and subsequently utilizing the cast to operatively position models of the patient's teeth in an articulator 122 are well known in the art.

In accordance with the present invention and with reference to FIG. 15, the teeth-simulating portions of the wax/stone models 118,120 are then reset to a desired orientation in accordance with a predetermined or prescribed arrangement. To this end, the portion of the wax 100 which surrounds a tooth-simulating portion desired to be moved is softened, as by brush-flaming the wax with an alcohol torch 124, and then the tooth-simulating portion is manually moved to the desired or preselected orientation. Once moved to the desired orientation, the tooth-simulating portion is carefully released so that the tooth-simulating portion does not shift or otherwise move from the desired orientation. Every tooth-simulating portion of each model 118 or 120 which is desired to be repositioned to a desired orientation is individually shifted in the aforedescribed manner. Upon completion of the repositioning of the teeth-simulating portions, the gum-simulating portion, indicated 126, of the wax/stone models 118,120 is built up and/or smoothed with wax as necessary to provide the models with the appearance of a healthy gum anatomy.

With the models 118,120 positioned within the articulator 122 so that the teeth-simulating portions are spaced a considerable distance apart, a relatively thick layer or wafer of wax is then inserted between the models and a reference wax interbite is taken to preserve the bite formation 118,120 of the models at a preselected vertical opening. It has been found that a vertical opening of the articulator within the range of about five to seven millimeters is satisfactory for purposes of this invention.

Figure 17:
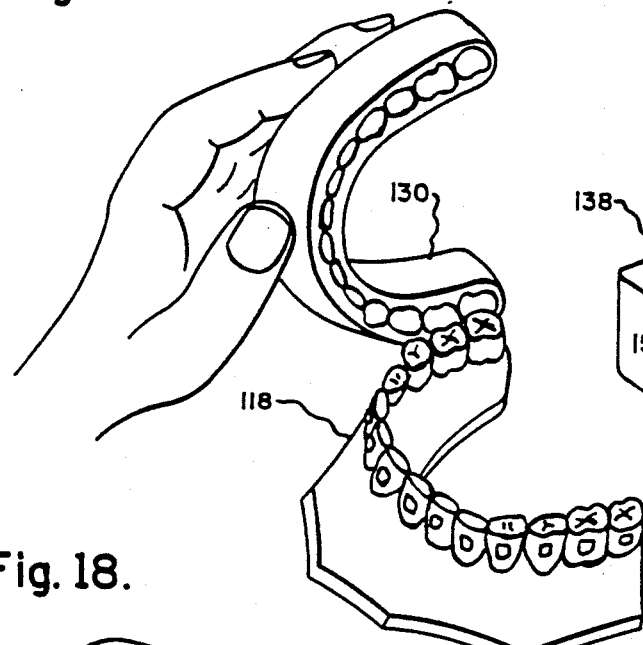
FIG. 17 is a perspective view of one of the models of FIG. 16 having its teeth-simulating portions arranged in a preselected orientation shown removed from the articulator and being utilized to form an impression of the teeth thereof when the teeth are oriented in the preselected orientation.

The models 118,120 are then removed from the articulator 122 and duplicated in die stone. The steps involved in duplicating the models 118,120 in die stone include steps indentical to those outlined above in connection with the obtaining of a die stone model of a patient's teeth. For example and in order to form a first construction model of one wax/stone model 118, an amount of BONDO SIL impression material is prepared and conformed into the shape of a cylinder, and the cylindrically-shaped amount is then placed upon the crowns of the teeth-simulating portions of the model 118 and pressed thereabout to shape the impression material about the detail of the teeth and retaining brackets simulated therein. The first amount of BONDO SIL is thereafter permitted to cure and a second amount of BONDO SIL impression material is thereafter applied in an overlying relationship with the cured first amount by means of a matrix fork. The second amount of impression material is thereafter permitted to cure, and as shown in FIG. 17, the cured impression, indicated 129, is removed from the wax/stone model. A uncured die stone composition is then brushed and spatulated within the formed impression 129 and permitted to cure to provide a hardened die stone construction model 130 (FIG. 18) of the wax/stone model 118. The construction model 130 is thereafter removed from the impression 129.

It will be understood that an impression can be formed of the wax/stone model 118 with an alginate composition in the manner outlined above in connection with the obtaining of an impression of the patient's upper dental arch for the purpose of forming the die stone construction model 130 of the wax/stone model 118. Briefly, an amount of alginate composition is seated about the teeth-simulating portions of the wax/stone model 118 and permitted to cure.

Upon completion of the first construction 130, a second construction model 132 (FIG. 18) is formed from the other wax/stone model 120 by forming the impression thereof with impression material and forming the die stone construction model 132 with the formed impression.

Figure 18:
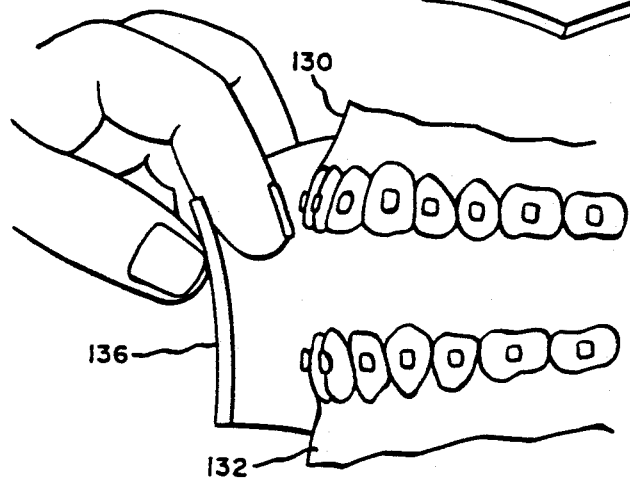
FIG. 18 is a plan view illustrating the building of a wax pattern about die stone construction models of the teeth of both the upper and lower dental arches when the teeth therein are oriented in a preselected orientation.
Figure 19:
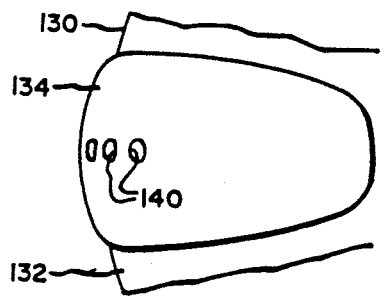
FIG. 19 is a plan view similar to that of FIG. 18 illustrating the wax pattern when completed about the die stone construction models.

With reference to FIGS. 18 and 19, the construction models 130,132 are thereafter used as a base or standard upon which a wax pattern 134 (FIG. 19) of the desired finishing positioner is formed. More specifically, the previously formed wax interbite taken while the wax/stone models were operatively mounted within the articulator 122 is operatively placed in overlying relationship with the construction model 130 and the construction model is operatively positioned upon the wax interbite. The resulting arrangement between the construction models 130,132 simulates the previously-obtained relationship between the wax/stone models 118,120 mounted within the articulator. To secure the relationship between the construction models, the peripheral edges of wax interbite are luted, or sealed with a heated instrument, to the construction models 130,132.

As illustrated in FIG. 18, additional wax is then applied to the inside and outside surfaces of the construction models in the form of heated wax sheets 136 (only one shown) to complete the wax pattern 134 (FIG. 19) of the positioner 22. If desired, the peripheral design of the positioner can be penciled or outlined upon the construction models to provide a visual border for the build-up of wax, and holes 140 can be carved into the wax pattern 134 as shown in FIG. 19 to provide breathing holes 51,51 (FIG. 1) in the desired positioner 22.

Figure 20:
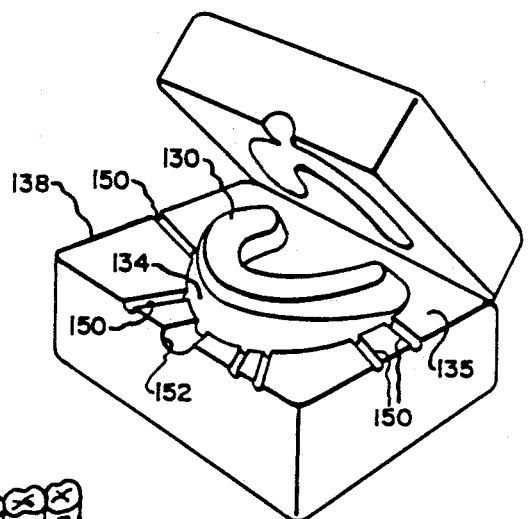
FIGS. 20 and 21 are perspective views of investment molding equipment being used to form a positioner with the completed wax pattern of FIG. 19.
Figure 21:
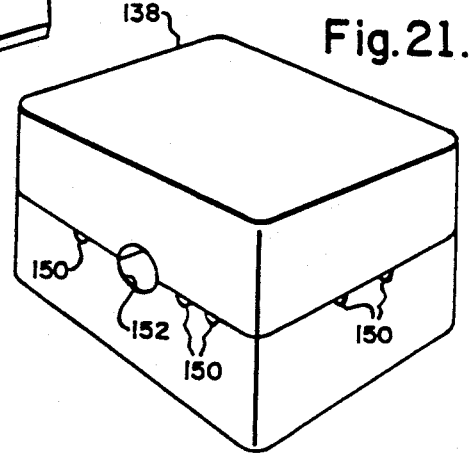
Figure 22:
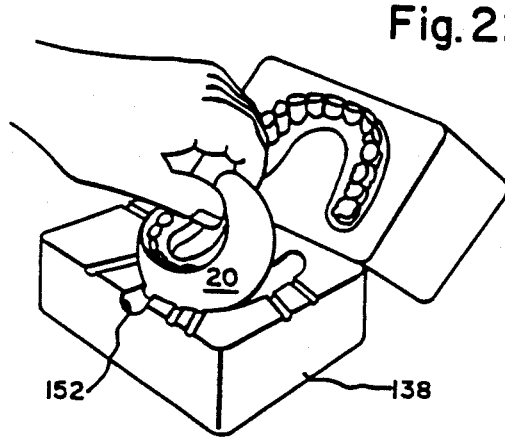
FIG. 22 is a perspective view illustrating the removal of a molded positioner from the molding equipment of FIGS. 21 and 22.

Upon completion of the wax pattern 134, the construction models 130,132, with the wax pattern 134 positioned thereabout, is used to mold the positioner 22. Such molding can be performed with investment molding equipment including an injection-type flask 138 illustrated in FIG. 20 and carried out by molding techniques which are well known in the art. Briefly and with reference to FIGS. 20–22, the construction models 130,132 and wax pattern 134 are operatively positioned in the injection-type flask 138, and a plaster investment 135 is poured around the models 130,132 and pattern 134. The wax pattern 134 is boiled out to define a mold cavity within the flask 138, and the wax pattern 134 is replaced with uncured elastomer base material, such as the aforementioned Dow Corning Q7-4840, injected into the mold cavity. After permitting the elastomer base material to cure to form the positioner 22, the positioner is removed from the flask 138 and finished, as by trimming with scissors and/or smoothing with a coarse wheel mounted in a bench lathe chuck, to remove material flash from vents and sprue of the mold. The finished positioner 22 is then ready for insertion into the patient's mouth.

To facilitate the investment molding of the positioner 22, it has been found that when investing the flask 138 with plaster, the flask be initially filled only to a height equal to about one-half the height of the wax pattern 134 when positioned within the flask 138. The investment is then allowed to set, and a separator is spread thereover before the second half of the investment is poured. The resultant mold or casting formed upon filling the remaining one-half of the flask 138 with investment is comprised of two mold halves. Furthermore, for purposes of permitting air to escape during the injection of the uncured elastomer base material, it is preferred that the mold cavity be vented by means of scored grooves 150 (FIG. 20) to the edge of the investment. A trench 152 is thereafter carved in the plaster to provide the main sprue through which elastomer is injected into the mold cavity. Still further, for purposes of preparing the mold cavity after boiling out the wax pattern 134, the mold halves are preferably dehydrated in a convection oven at about 150° Fahrenheit for about two hours. After dehydration, an alginate base separator is applied to the molds, and the mold halves are secured and ready for injection.

With injection molding completed, the elastomer base material, and in particular, Dow Corning Q7-4840 is cured by placing the filled mold within a heated, dry pressure vessel maintained at about 275° Fahrenheit and leaving the mold in the vessel for about three hours. The mold is then removed from the vessel and permitted to bench cool for about twenty minutes. The mold halves are then separated by hand to permit access to the molded positioner 22.

Although the positioner 20 of FIGS. 1-3 has been shown and described as including breathing holes 51,51 defined in the mid-portion 34 of the positioner 20, it will be understood that a positioner in accordance with the present invention need not have such holes.

Figure 23:
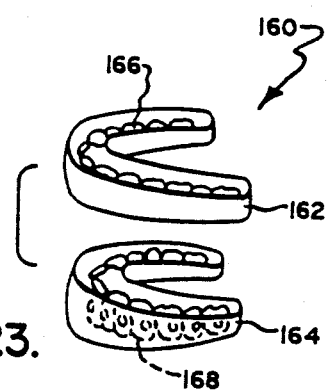
FIG. 23 is a perspective view of an alternative embodiment of the positioner in accordance with this invention.

Furthermore, inasmuch as the positioner 20 of FIGS. 1-3 is a full positioner in that it is adapted to receive the teeth and brackets of both the upper and lower arch of the patient, it will be understood that a positioner in accordance with the present invention can be a two-part or split positioner wherein each part is adapted to closely receive the teeth and brackets of a corresponding one of the dental arches. For example, there is shown in FIG. 23 a split positioner 160 comprised of two body parts 162 and 164, each having a recess 166 or 168, respectively, adapted to closely receive the teeth of a corresponding dental arch and urge the teeth to a predetermined occlusion when operatively placed thereabout. The steps involved in constructing the split positioner 160 are the same as those involved in constructing the positioner 20 of FIGS. 1-3 through the steps of providing construction models of the wax/stone models. Separate wax patterns are thereafter built upon each construction model to yield a pair of pattern-bearing construction models. Preferably, the wax patterns are indexed with one another to ensure proper fit-up of the resultant positioner parts within the mouth. Each construction model, with its corresponding wax pattern, is then used to investment mold a corresponding one of the parts 162 or 164.

Still further, although the interior surface 47 or 53 of the indentations 46 or 50, repsectively, of the positioner 20 of FIGS. 1-3 have been shown and described as being defined by the elastomeric base material of the positioner body 22, the interior surface of the body indentations may be defined by other means in accordance with the broader aspects of this invention. For example, there is shown in FIG. 24, an alternative positioner 170 having a body 172 in which is defined a recess 174 and an associated indentation 176 for nestingly receiving the teeth J and tooth-mounted coupling member 178, respectively. The indentation 176 defines an interior surface 180 provided by a cup-like liner 182 secured within the positioner body 172. The cup-like liner 182 is preferably constructed of a relatively rigid material such as a hard plastic and includes integral wings 181,181 embedded within the body 172 for securing the liner 182 therein. When the positioner 172 is operatively positioned upon the teeth J so that the cup-like liner 182 nestingly accepts and thereby completely encircles the coupling member 178 in a snap-fit arrangement, the liner 182 and member 178 coact as female and male couplers, respectfully, to releasably secure the body 172 to the teeth J. Furthermore, because the liner 182 is relatively rigid, the liner 182 is believed to enhance the fit-up relationship between the teeth J and body 172 and further enhance the transfer of elastic force potential of the body 172 to the teeth J.

In order to construct the positioner 170 of FIG. 24 so that the liner 182 is operatively secured within the positioner body 172, the liner 182 is operatively positioned upon the die stone construction model prior to the build-up of a wax pattern of the positioner body thereabout. The die stone construction model will, of course, in accordance with the method of this invention include a portion simulating the coupling member 178, and the liner 182 is operatively positioned about such a coupling member-simulating portion. The wax pattern of the positioner body is then built upon the construction model so that the liner 182 is effectively set within the wax pattern. When the wax pattern is subsequently replaced by elastomer base material in an injection molding process to form the positioner body 172, the liner 182 is effectively secured within the positioner body 172. It will be understood that the embedding of the integral wings 181,181 within the elastomer body 172 of the positioner 170 enhances the retention of the liner 182 by the body 172.

Yet still further, although the steps of the aforedescribed method embodiment illustrated in FIGS. 5a and 5b and involving the covering or wrapping of the brackets 28,28 may, in the case of some types of brackets, be eliminated in the broader aspects of the method of this invention. For example, there is illustrated in FIG. 25, a coupling member 184 in the form of a bracket 186 operatively secured to a tooth K. Such a bracket 186, available from Kreative Koncepts Inc., Hinsdale, Ill. under the trademark designation LO-SHOW ESTHETIC BRACKETS, possesses no sharp edges which could damage an impression upon removal of the impression therefrom or defines any undercut in which impression material could become lodged.

Further still, although the steps illustrated in FIGS. 6–12 involved to construct a die stone facsimile 88 of the patient's upper arch including a step of applying impression material directly to the teeth and brackets when positioned within the mouth, alternative steps can be employed for obtaining the die stone facsimile. For example and with reference FIGS. 26–29, there are illustrated alternative steps for obtaining a coupling member-bearing die stone facsimile 192 (FIG. 28) for a set of teeth L (FIG. 26) of a patient's upper dental arch to which coupling members have yet to be attached and for which a positioner in accordance with the present invention is desired to be fabricated. To obtain the facsimile 192, a dental impression or cast of the teeth L is initially obtained in the manner illustrated in FIG. 26, and the obtained dental impression is used to build a die stone facsimile 190 (FIG. 27) of the teeth L. The dental cast is constructed of plaster, and the steps involved in obtaining such an impression and subsequently forming a dental facsimile are well known in the art. Accordingly, a detailed discussion of such steps are believed to be unnecessary. Coupling members such as brackets 28,28, are then attached as shown in FIG. 27 to the teeth-simulating portions of the facsimile to provide the coupling member-bearing facsimile 192 (FIG. 28). The coupling members 28 are attached to the facsimile 192 with a temporary glue or wax and are attached at locations thereon corresponding to the locations upon the teeth L to which coupling members 28 are desired to be attached.

With reference still to FIG. 28, a transfer matrix 194 is then formed by means of a Bondo Sil impression of the coupling member-bearing facsimile 192. The Bondo Sil impression, when cured and removed from the facsimile 192, is the transfer matrix 194. Subsequently, the coupling member-bearing facsimile 192 is used as a standard or guide for the construction of a wax/stone model having teeth-simulating portions therein reset to a desired orientation. For example, the teeth-simulating portions of the facsimile 192 can be either separated and repositioned in accordance with the steps illustrated in FIGS. 12–16 to obtain the desired die stone facsimile or the facsimile 192 can be duplicated in die stone and then the teeth-simulating portions of the duplication can be separated and repositioned in accordance with the steps of FIGS. 12–16. The desired positioner is thereafter formed in conformity to the shape of the coupling member-bearing facsimile 192 by, for example, the steps illustrated in FIGS. 17–22.

When the facsimile 192 is no longer needed for positioner-forming purposes, the coupling members 28,28 are removed from the facsimile 192 and transferred to the matrix 194. By means of the matrix 194, and with reference to FIG. 29, the brackets 28,28 are transferred to the teeth L of the patient and cemented in place. The formed positioner can then be positioned about the teeth L for operative coaction with the brackets 28,28. For a more detailed description of the steps involved in the indirect transfer of coupling members to a patient, reference can be made to U.S. Pat. No. 3,738,005 incorporated herein by reference.

It will be understood that numerous modifications and substitutions can be had to the aforedescribed embodiments without departing from the spirit of the invention. For example, although the material out of which the positioner is constructed has been described as an elastomer base material providing the body with a degree of flexibility, resiliency and elasticity, it will be understood that the durometer or firmness of the elastomer base material may be within a range of durometer levels. In some teeth-repositioning applications, for example, it may be desirous to move teeth to an ultimately-desired orientation during two stages wherein teeth are moved from an initial maloccluded orientation to an intermediate orientation by means of a first positioner and the teeth are moved from the intermediate orientation to the ultimately-desired orientation by means of a second positioner. In such applications, the durometer of the first positioner may be different from the durometer of the second positioner. Accordingly, the aforedescribed embodiments are intended for the purposes of illustration and not as limitation.

We claim:

1. A method of constructing an orthodontic positioner for maloccluded teeth located in a preselected one of the upper and lower dental arches of a patient for placing in position in the patient's mouth for contact with the patient's teeth and for contact and coaction with teeth-mounted coupling members, of:

said positioner acting against the teeth and coupling members to effectively bias the teeth of the one arch toward a preselected orientation, said method comprising the steps providing a hardened dental facsimile formed from an impression of the preselected dental arch wherein the dental facsimile includes portions simulating the teeth and a portion of the gum tissue adjacent the teeth of the preselected dental arch and the surfaces of the coupling members are defined by the surfaces of either coupling member-simulating portions of the facsimile formed by the impression or coupling members attached to the teeth-simulating portions of the facsimile;

repositioning teeth-simulating portions of the dental facsimile to a preselected orientation so as to provide a first model of the preselected dental arch having teeth-simulating portions oriented in the same manner as the teeth in the preselected arch are desired to be oriented;

providing an amount of elastomer base material; and forming the positioner out of said elastomer base material so that said positioner assumes a resilient, elastic and flexible body having an arcuate-shaped portion along which is defined a recess having walls of substantial thickness defining teeth-engaging surfaces for receiving the teeth-simulating portions of said first model and a series of indentations disposed across said teeth-engaging surfaces wherein each indentation is shaped to nestingly accept a corresponding coupling member surface defined upon said first model so that when the positioner body is operatively placed in position in the patient's mouth, the positioner body acts against the teeth and coupling members to effectively bias the teeth of the one arch toward the preselected orientation.

2. A method as defined in claim 1 wherein said step of providing a dental facsimile is preceded by the steps of:

providing an amount of uncured impression material suitable for accurately capturing the shape of the patient's teeth and of the coupling members when applied thereto and which, when cured, possesses a degree of flexibility;

selectively applying said amount of impression material to the preselected arch or a model thereof so that said impression material generally conforms to the shape of the teeth of the preselected dental arch, coupling members and a portion of the gum tissue adjacent the teeth or a model thereof;

permitting said amount of impression material to cure so that an enduring impression of the teeth, coupling members and gum tissue of the preselected dental arch is formed in one side of said amount;

removing the enduring impression from the preselected dental arch or a model thereof;

providing an amount of high strength die stone in an uncured condition and filling the enduring impression with said amount of die stone; and permitting said amount of die stone to cure to thereby provide the hardened dental facsimile of the teeth, coupling members and a portion of the gum tissue of the preselected dental arch; and removing said enduring impression from said hardened facsimile.

3. A method as defined in claim 2 wherein said coupling members are operatively mounted upon the teeth in said one dental arch prior to the forming of said enduring impression and said step of applying said amount of impression material operatively positions the teeth, coupling members and said gum tissue portion of the preselected arch in the patient's mouth.

4. A method as defined in claim 2 wherein said teeth of said preselected dental arch are absent the coupling members prior to the forming of said enduring impression and said step of applying said amount of impression material is preceded by the steps of:

making a dental cast of the preselected dental arch;

forming a hardened model of the preselected dental arch with said dental cast; and operatively positioning the coupling members upon the teeth of said hardened model.

5. The method of claim 4 wherein said step of forming the positioner is followed by the steps of:

removing the coupling members from the hardened facsimile; and operatively attaching the coupling members to the teeth of a preselected dental arch in the patient's mouth in the same position in relationship to the teeth that the coupling members assumed when positioned upon the teeth of said hardened model.

6. The method as defined in claim 2 wherein said amount of impression material is a first amount and said step of permitting said first amount of impression material to cure is followed by the step of:

providing a second amount of uncured impression material and pressingly applying said second amount to the side of said first amount generally opposite said one side thereof so that said second amount extends substantially along the entire length of the arc of said first amount and so that said second amount fixedly adheres to said first amount;

permitting said second amount to cure so that said cured first and second amounts form a unitary impression of the preselected dental arch wherein said unitary impression provides said enduring impression.

7. A method as defined in claim 2 wherein said step of repositioning teeth-simulating portions includes the steps of:

separating portions of said facsimile simulating preselected ones of the patient's teeth desired to be repositioned to a predetermined orientation from the remainder of the facsimile and returning each separated teeth-simulating portion to the enduring impression and into substantially its original position when formed therein;

applying wax to the teeth-simulating portions positioned within the enduring impression to secure the separated teeth-simulating portions to one another and to thereby provide a reconstructed facsimile of said preselected dental arch;

applying an amount of die stone to the applied wax for providing a base for said reconstructed facsimile and to thereby form a first combination wax/stone model simulating the preselected dental arch;

removing said first combination wax/stone model from said enduring impression; and resetting each teeth-simulating portion of said first combination wax/stone model desired to be repositioned to a predetermined orientation by warming the wax surrounding the teeth-simulating portions of said first wax/stone model to thereby loosen said teeth-simulating portions and shifting the teeth-simulating portions to a predetermined orientation;

8. A method as defined in claim 7 wherein said step of forming the positioner includes the steps of:

duplicating said first wax/stone model in die stone so as to form a construction model of the patient's teeth, coupling members and portion of the gum tissue in the preselected dental arch when the teeth therein are positioned in the predetermined orientation;

building a wax pattern of the desired positioner upon said construction model so as to provide a pattern-supporting construction model, which positioner includes a part adapted to be positioned about at least the teeth, coupling members and gum tissue portion of the preselected dental arch;

providing investment molding equipment and an uncured amount of elastomer base material out of which the positioner is to be constructed, operatively positioning the pattern-supporting construction model within the investment molding equipment and utilizing investment molding techniques to replace the wax pattern within the molding equipment with the uncured amount of elastomer base material;

permitting the amount of elastomer base material to cure to thereby provide the positioner; and removing the positioner from the investment molding equipment.

9. A method as defined in claim 2 wherein said step of applying said amount of impression material is preceded by the step of covering each coupling member of the preselected arch so that impression material subsequently applied to and permitted to cure about the teeth and coupling members is not appreciably damaged by the coupling members upon removal of the cured impression from the teeth and coupling members.

10. The method of claim 1 wherein said step of repositioning teeth-simulating portions of the dental facsimile is followed by the steps of:

providing a relatively rigid liner for coacting with a coupling member in a male/female coupling arrangement;

operatively positioning the liner about surfaces of the defined coupling members;

operatively positioning the liner so that the subsequent step of forming the positioner includes a step of shaping the elastomer base material about the liner so that the defined indentation of the positioner body is effectively lined by the liner.

11. The method of claim 10 wherein said liner has integral retention wings and the step of shaping the elastomer base material embeds the integral retention wings within the base material to effectively secure the liner within the positioner body.

12. A method of constructing an orthodontic positioner for maloccluded teeth located in a preselected one of the upper and lower dental arches of a patient for coaction with teeth-mounted coupling members including portions protruding from the sides of the teeth, (a) providing an amount of uncured impression material suitable for accurately capturing the shape of the patient's teeth and of the coupling members when applied thereto and which, when cured, possesses a degree of flexibility;

(b) selectively applying said amount of impression material to the preselected arch or a model thereof so that said impression material generally conforms to the shape of the teeth of the preselected dental arch, coupling members and a portion of the gum tissue adjacent the teeth;

(c) permitting said amount of impression material to cure so that an enduring impression of the teeth, coupling member protruding portions and gum tissue of the preselected dental arch is formed in one side of said amount;

(d) removing the enduring impression from the preselected dental arch or the model thereof;

(e) providing an amount of high strength die stone in an uncured condition and filling the enduring impression with said amount of die stone;

(f) permitting said amount of die stone to cure to thereby provide a hardened facsimile of the teeth, coupling member protruding portions and a portion of the gum tissue of the preselected dental arch or a model thereof;

(g) removing said enduring impression from said hardened facsimile;

(h) separating portions of said hardened facsimile which simulate preselected ones of the patient's teeth desired to be repositioned to a predetermined orientation from the remainder of the facsimile and returning each separated teeth-simulating portion to the enduring impression and into substantially its original position when formed therein;

(i) applying wax to the teeth-simulating portions positioned within the enduring impression to secure the separated teeth-simulating portions to one another and to thereby provide a reconstructed facsimile of said preselected dental arch;

(j) applying an amount of die stone to the applied wax for providing a base for said reconstructed facsimile and to thereby form a first combination wax/stone model simulating the preselected dental arch;

(k) removing said first combination wax/stone model from said enduring impression;

(l) repeating steps (a) through (k), inclusively, with the other of the preselected ones of the upper and lower dental arches of the patient to form a second combination wax/stone model simulating the other dental arch, (m) providing a dental articulator and operatively mounting said first and second combination wax/stone models upon said articulator so that said first and second wax/stone models simulate the actual indexed relationship of the upper and lower dental arches of the patient;

(n) resetting each tooth-simulating portion of said first combination wax/stone model desired to be repositioned to a predetermined orientation by warming the wax surrounding the tooth-simulating portions of said first wax/stone model to thereby loosen said tooth-simulating portions and shifting the tooth-simulating portions to a predetermined orientation;

(o) removing said first wax/stone model from the articulator;

(p) duplicating said first wax/stone model in die stone so as to form a construction model of the patient's teeth, protruding portions of the coupling members and portion of the gum tissue in the preselected dental arch when the teeth therein are positioned in the predetermined orientation;

(q) building a wax pattern of the desired positioner upon said construction model so as to provide a pattern-supporting construction model, which positioner includes a part adapted to be positioned about at least the teeth, protruding portions of the coupling members and gum tissue portion of the preselected dental arch;

(r) providing investment molding equipment and an uncured amount of elastomer base material out of which the positioner is to be constructed;

(s) operatively positioning the pattern-supporting construction model within the investment molding equipment and utilizing investment molding techniques to replace the wax pattern within the molding equipment with the uncured amount of elastomer base material;

(t) permitting the amount of elastomer base material to cure to thereby provide the positioner; and (u) removing the positioner from the investment molding equipment.

13. The method as defined in claim 12 wherein said step of duplicating said first wax/stone model in die stone includes a repeat of steps (a) through (g), inclusively, with said first wax/stone model.

14. The method as defined in claim 12 wherein said step of removing the positioner from the investment molding equipment is followed by the step of removing any undesired base material from said positioner to thereby finish the positioner.

15. The method of claim 12 wherein the positioner part built upon the construction model out of wax is adapted to be positioned about only the teeth, coupling member protruding portions and portion of gum tissue of the preselected dental arch and said step of mounting said first and second combination wax/stone models upon said articulator is followed by the steps of:

resetting each tooth-simulating portion of said second combination wax/stone model desired to be repositioned to a preselected orientation by warming the wax surrounding the tooth-simulating portions of said second wax/stone model to thereby loosen the tooth-simulating portions and shifting the tooth-simulating portions of the second wax/stone model to a preselected orientation;

removing said second wax/stone model from the articulator;

duplicating said second wax/stone model in die stone so as to form a construction model of the patient's teeth and portion of the gum tissue in the other dental arch when the teeth therein are positioned in the preselected orientation; and building a wax pattern of the remaining part of the desired positioner upon said second construction model about the teeth and portion of gum tissue;

utilizing investment molding techniques to injection-mold the remaining positioner part.

16. The method of claim 15 wherein said steps of building a wax pattern of the desired positioner upon said construction models includes the steps of operatively positioning the first and second construction models in operative indexed and open-bite relationship with one another so that the wax pattern subsequently build upon the construction models simulates a full positioner adapted to receive the teeth of both the upper and lower dental arch.

17. The method of claim 16 wherein said step of building a wax pattern upon said construction models includes a step of carving holes in said pattern to provide holes in the subsequently formed positioner to facilitate breathing when the positioner is operatively worn.

18. A method of constructing an orthodontic positioner for maloccluded teeth located in a preselected one of the upper and lower dental arches of a patient for coaction with teeth-mounted coupling members including portions protruding from the sides of the teeth including the steps of:

providing a construction model of the patient's teeth, the teeth-mounted coupling members, and a portion of the gum tissue in the preselected dental arch when the teeth therein are positioned in a desired orientation;

builing a wax pattern of the desired positioner upon said construction model so as to provide a pattern-supporting construction model, which positioner includes a part adapted to be positioned about at least the teeth, protruding portions of the coupling members and gum tissue portion of the preselected dental arch;

providing investment molding equipment and an uncured amount of elastomer base material out of which the positioner is to be constructed;

operatively positioning the pattern-supporting construction model within the investment molding equipment and utilizing investment molding techniques to replace the wax pattern within the molding equipment with the uncured amount of elastomer base material;

permitting the amount of elastomer base material to cure to thereby provide the positioner, wherein the positioner includes an arcuate portion along which is defined a recess having walls defining teeth-engaging surfaces for receiving the teeth of the patient and a series of indentations disposed across said teeth-engaging surfaces wherein each indentation is shaped to nestingly accept the protruding portions of the coupling members; and removing the positioner from the investment molding equipment.

* * * * *